US012733893B2

(12) United States Patent
Gold et al.

(10) Patent No.: US 12,733,893 B2
(45) Date of Patent: Sep. 15, 2026

(54) METHOD FOR RIGID MOTION CORRECTION OF PET AND MR IMAGES ON PET/MR SCANNERS

(71) Applicant: The Board of Trustees of the Leland Stanford Junior University, Stanford, CA (US)

(72) Inventors: Garry E. Gold, Stanford, CA (US); Farshad Moradi, San Diego, CA (US); Mohammad Mehdi Khalighi, San Jose, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 19/186,030

(22) Filed: Apr. 22, 2025

(65) Prior Publication Data

US 2025/0325243 A1 Oct. 23, 2025

Related U.S. Application Data

(60) Provisional application No. 63/637,510, filed on Apr. 23, 2024.

(51) Int. Cl.

| | |
|---|---|
| ***A61B 6/00*** | (2024.01) |
| ***A61B 6/03*** | (2006.01) |
| ***G01R 33/48*** | (2006.01) |
| ***G01R 33/565*** | (2006.01) |

(52) U.S. Cl.

CPC ............ *A61B 6/5247* (2013.01); *A61B 6/037* (2013.01); *G01R 33/481* (2013.01); *G01R 33/56509* (2013.01)

(58) Field of Classification Search

CPC ...... A61B 6/5247; A61B 6/037; G01R 33/481

See application file for complete search history.

(56) References Cited

U.S. PATENT DOCUMENTS

| | | | | |
|---|---|---|---|---|
| 11,672,492 | B2 | 6/2023 | Khalighi | |
| 2019/0101655 | A1* | 4/2019 | Wang | G01R 33/28 |
| 2020/0211237 | A1* | 7/2020 | Feng | G06T 12/20 |

FOREIGN PATENT DOCUMENTS

CN 114299183 A * 4/2022

OTHER PUBLICATIONS

Fakhre Alam et al., Challenges and Solutions in Multimodal Medical Image Subregion Detection and Registration, Journal of Medical Imaging and Radiation Sciences, vol. 50, Issue 1, 2019, pp. 24-30 (Year: 2018).*

F Godenschweger et al., Motion correction in MRI of the brain, Physics in Medicine & Biology, vol. 61, No. 5, Published Feb. 11, 2016, p. R32-R56 (Year: 2016).*

Spangler-Bickell et al., Rigid Motion Correction for Brain PET/MR Imaging using Optical Tracking. IEEE Trans Radiat Plasma Med Sci actions. Jul. 2019;3(4):498-503.

(Continued)

*Primary Examiner* — Chao Sheng

(74) *Attorney, Agent, or Firm* — LUMEN PATENT FIRM

(57) ABSTRACT

A method for combined PET/MR imaging performs a PET/MR scan using a PET/MR scanner. During the scan a frame is reconstructed and co-registered with a reference frame. The reference frame is dynamically updated throughout the PET/MR scan by incorporating most recently co-registered images from previously reconstructed frames.

4 Claims, 10 Drawing Sheets

(56) References Cited

OTHER PUBLICATIONS

Keller et al., Motion correction in simultaneous PET/MR brain imaging using sparsely sampled MR navigators: a clinically feasible tool. EJNMMI Physics, vol. 2, No. 14 (2015).
Khalighi et al., "High Quality Isotropic Whole-body PET Imaging Using MR Priors," J Nucl Med May 2020 vol. 61 supplement 1.

* cited by examiner

300
Is this the end of a repetition time (TR) in MR.
yes
no
302 Wait till the end of TR.
304 Read the latest motion transfer function provided by simultaneous PET acquisition.
306 Use the motion transfer functions to update MR gradient waveforms for motion correction.

Translations
X
Y
Z
(mm)
7
6
5
4
3
2
1
0
-1
0
500
1000
1500
2000
2500
3000
3500
Time (s)

Translations
X
Y
Z
(mm)
2
1.5
1
0.5
0
-0.5
-1
0
500
1000
1500
2000
2500
3000
3500
Time (s)

Translations
Translation (mm)
4
2
0
-2
-4
X
Y
Z
0
500
1000
1500
2000
Time (s)

Translations
Translation (mm)
2
1
0
-1
-2
-3
X
Y
Z
0
500
1000
1500
2000
Time (s)

METHOD FOR RIGID MOTION CORRECTION OF PET AND MR IMAGES ON PET/MR SCANNERS

CROSS-REFERENCE TO RELATED APPLICATIONS

This application claims priority from U.S. Provisional Patent Application 63/637,510 filed Apr. 23, 2024, which is incorporated herein by reference.

STATEMENT OF FEDERALLY SPONSORED RESEARCH

None.

FIELD OF THE INVENTION

The present invention relates generally to medical imaging. More specifically, it relates to methods for rigid motion correction in combined PET/MR imaging.

BACKGROUND OF THE INVENTION

Combined PET/MR imaging is a powerful tool in neuroscience and oncology, particularly for diagnosing neurodegenerative diseases such as dementia and Parkinson's disease, and for pain imaging. It combines the strengths of both PET and MRI, providing detailed functional images of brain activity through PET and high-resolution anatomical images through MRI.

A combined PET/MR imaging apparatus typically includes a PET scanner, an MRI scanner, and an imaging workstation. The PET scanner uses a radiotracer to detect gamma rays emitted during positron decay, while the MRI scanner uses magnetic fields and radio waves to provide anatomical detail.

Combined PET/MR reduces patient exposure to ionizing radiation compared to PET/CT. Additionally, MRI images can be used as priors for PET reconstruction, leading to higher quality and spatially accurate PET images.

A significant challenge in PET/MR imaging is motion artifact due to patient motion during the scan. These motion artifacts can reduce the accuracy of both PET and MRI data. Recent research efforts are focusing on advanced motion correction techniques to address this limitation and further unlock the potential of PET/MR imaging. Existing methods, however, only provide motion correction in static head PET imaging.

Various methods have been developed to address motion artifacts in MR imaging, with prospective motion correction techniques emerging as a promising approach. These methods aim to correct for motion in real-time during the MR sequence itself, potentially leading to more accurate and artifact-free images. However, they necessitate near-real-time motion tracking to enable timely updates to the MR sequence within each repetition time (TR). One effective strategy for real-time motion tracking involves the use of an optical camera system. This approach typically involves a marker or patch placed on the subject's forehead, which is tracked by the camera to precisely measure head motion. The captured motion data is then integrated with the MR system to dynamically adjust the imaging sequence, mitigating the effects of motion. In this approach, the camera is typically mounted on the head coil to monitor patient motion and it attenuates the PET signal causing degradation in PET brain images quality.

One approach to motion correction in PET image reconstruction involves co-registering multiple short-frame PET images. This technique aims to align frames that may have been affected by patient motion and to estimate the motion transfer function for the whole PET exam which is used later in a list-mode PET reconstruction for PET motion correction. However, in this approach, only a single reference frame is used as the basis for co-registration. This approach also assumes a relatively stable tracer distribution throughout the PET exam. Consequently, it may not be optimal for cases where the tracer distribution undergoes significant changes during the acquisition, such as when imaging commences immediately after tracer injection.

SUMMARY OF THE INVENTION

The present method provides a method for MR motion correction on PET/MR images, and includes dynamic PET imaging in imaging head and legs. Unlike previous methods that rely on a single, static reference frame, our approach dynamically updates the reference frame throughout the scan to account for evolving tracer distribution. Specifically, after each new frame is co-registered, the reference frame is regenerated by incorporating the most recently co-registered images from previous frames. This adaptive approach ensures that the reference frame remains closely aligned with the current tracer distribution, even as it undergoes significant changes during the acquisition. By maintaining this close alignment, the method provides a substantial improvement in registration accuracy compared to methods that utilize a fixed reference frame.

The present method provides techniques for rigid body motion correction on PET/MR scanners including several advantageous features. It can provide motion correction in dynamic PET imaging where the tracer distribution changes during the scan. It performs optimization of rigid head motion correction. It provides rigid motion correction for legs in PET/MR scans. It provides rigid motion correction of MR images in PET/MR, facilitated by using real-time reconstruction of short PET frames. This technique can be used on any commercial combined PET/MR scanners such as those offered by GE HealthCare, Siemens Healthineers or United Imaging.

To address motion artifacts in PET imaging, we here disclose a motion correction method that dynamically updates the reference frame throughout the scan to account for evolving tracer distribution. Specifically, after each new frame is co-registered, the reference frame is regenerated by incorporating the most recently co-registered images from previous frames. This adaptive approach ensures that the reference frame remains closely aligned with the current tracer distribution, even as it undergoes significant changes during the acquisition. By maintaining this close alignment, it provides a substantial improvement in registration accuracy compared to methods that utilize a fixed reference frame.

In one aspect, the invention provides a method for combined PET/MR imaging, the method comprising: performing a PET/MR scan using a PET/MR scanner, wherein performing the PET/MR scan comprises: a) reconstructing by the PET/MR scanner a frame and co-registering the frame with a reference frame; and b) dynamically updating by the PET/MR scanner the reference frame throughout the PET/MR scan by incorporating most recently co-registered images from previously reconstructed frames. The reconstructing the frame and co-registering the frame may include a) initially estimating Tz and Tx by co-registering a current frame to the reference frame; and b) subsequently estimating Ty, Rx, Ry, and Rz. The reconstructing the frame and co-registering the frame may include dividing the frame and the reference frame with a sagittal plane in two equal sections, and co-registering the two sections independently. The dynamically updating by the PET/MR scanner the reference frame throughout the PET/MR scan may include estimating a motion transfer function from short PET frames live on the PET/MR scanner and using the motion transfer function in an MRI sequence to update gradient waveforms and correct for patient motion.

DETAILED DESCRIPTION OF THE INVENTION

Figure 1:
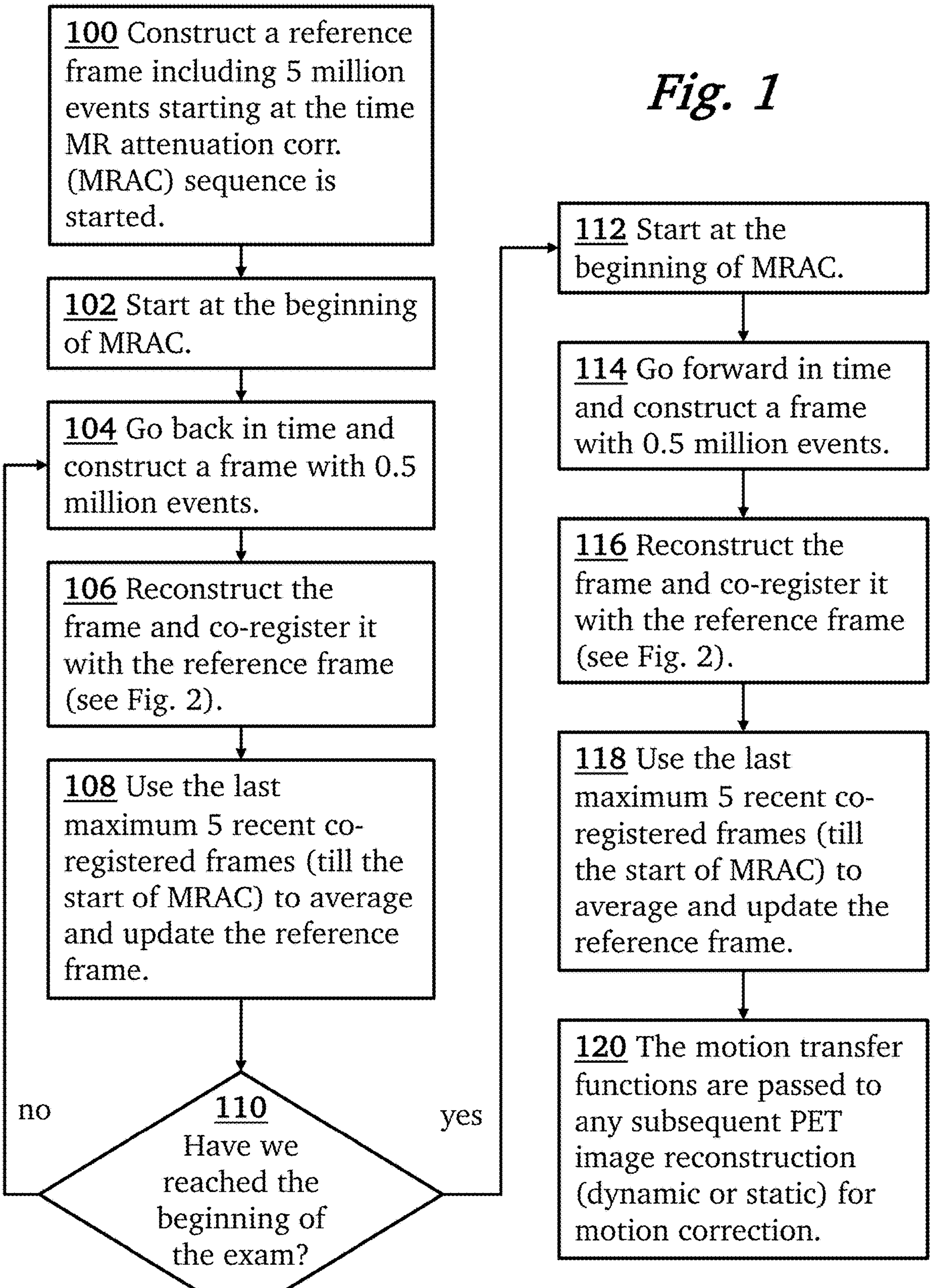
FIG. 1 is a flowchart outlining steps of a method for rigid motion correction, according to an embodiment of the invention.

In rigid motion correction for head imaging, precise co-registration involves the estimation of six parameters: three rotations (Rx, Ry, Rz) and three translations (Tx, Ty, Tz). To enhance accuracy, embodiments of the invention provide a prioritized estimation approach that capitalizes on the characteristic patterns of head motion in PET/MR imaging.

The inventors discovered that ~70% of motion occurs in head moving up/down or right/left in the head coil. Based on this, embodiments of the invention initially estimate the two parameters most susceptible to significant motion in PET/MR: Tz (translation along the Z-axis, corresponding to patient head movement up or down) and Tx (translation along the X-axis, corresponding to patient head movement right or left). Subsequently, we estimate the remaining four parameters: Ty, Rx (known as Pitch head movement), Ry (known as Roll head movement), and Rz (known as Yaw head movement). These typically exhibit minimal motion due to the head coil's constraints, allowing for more accurate estimation after the dominant motions are addressed. By prioritizing the parameters most prone to substantial motion, we mitigate the potential for error propagation that could compromise the estimation of other parameters. We anticipate that this prioritized estimation approach will significantly improve the accuracy of co-registration between frames and the reference frame, leading to more precise motion correction and enhanced image quality.

In situations where motion correction for the legs is desired in PET/MR imaging, embodiments of the invention are based on dividing the field of view (FOV) into two equal sections. This division is achieved by placing a sagittal plane in the center, running from the hip joint down to the feet. We've developed this approach based on the observation that each leg movement during PET/MR scans can be treated as a distinct rigid body, except for knee flexion. However, knee flexion is not the main source of motion in PET/MR imaging. This is because the knees are typically either resting on an angled foam for comfort or, in the case of knee imaging, they are secured within the imaging coil for clearer scans. By treating each leg as a separate rigid body, we achieve more accurate motion correction by estimating and applying individualized transfer functions for each section. This avoids the limitations of single, global transfer functions which might struggle to capture the nuances of independent leg motion. Independent correction allows for a more precise representation of the actual motion occurring in each leg, leading to enhanced overall image quality. Global transfer functions are susceptible to error propagation across both legs, potentially distorting the final image. Independent correction minimizes this risk, ensuring higher fidelity in the outcome. Overall, this method corrects for leg motion artifacts in PET/MR imaging, leading to more accurate and diagnostically valuable images.

Embodiments of the present invention for real-time MR motion correction in PET/MR imaging leverages PET data directly for motion estimation, eliminating the need for external camera systems. This approach integrates seamlessly with simultaneous PET/MR acquisition. PET data is continuously analyzed during the scan to estimate motion transfer functions in almost real-time. The estimated motion transfer functions are promptly passed to the concurrently running MR sequence. This enables real-time updates to the MR gradient waveforms, adapting the MR acquisition to compensate for detected motion. Unlike previous prospective motion correction methods that rely on external coils or cameras, this approach harnesses the intrinsic motion information already present within the PET data. This eliminates the need for additional hardware and simplifies the process. The ability to estimate and apply motion corrections in real-time during the scan holds significant potential for mitigating motion artifacts before they can compromise image quality. The combination of PET-derived motion information and real-time MR sequence updates is expected to produce MR images with improved sharpness and accuracy, even in the presence of patient movement. The elimination of external cameras streamlines the imaging setup and reduces the potential for errors or technical challenges associated with camera systems.

By using an adaptive frame instead of a single frame, the present approach improves rigid motion correction in dynamic PET imaging. By first estimating the dominant motion in PET/MR brain imaging (i.e., the displacement Tx in X direction, corresponding to patient head movement right or left, and the displacement Tz in Z direction, corresponding to patient head movement up or down), the method achieves a robust registration. By dividing the body images for legs with a sagittal plane, motion in each section can be treated as rigid body motion and the rigid motion correction method can be applied to each section individually. The motion transfer function can be estimated from short PET frames live on the PET/MR scanner and passed on to the simultaneously run MRI sequence to update the gradient waveforms and correct for patient motion.

FIG. 1 is a flowchart outlining steps of a method for rigid motion correction, according to an embodiment of the invention. These steps are performed in the context of a method for combined PET/MR imaging. A PET/MR scan is performed using a PET/MR scanner. The PET/MR scan includes reconstructing a frame and co-registering the frame with a reference frame; and dynamically updating the reference frame throughout the PET/MR scan by incorporating most recently co-registered images from previously reconstructed frames. More specifically, in step 100 a reference frame is constructed including 5 million events starting at the time MR attenuation corr. (MRAC) sequence is started. In step 102 the start of MRAC begins. In step 104 Go back in time and construct a frame with 0.5 million events. In step 106 the frame is reconstructed and co-registered with the reference frame and the motion transfer function is recorded (for details see FIG. 2). In step 108 the last maximum 5 recent co-registered frames (till the start of MRAC) are used to average and update the reference frame. In step 110 if we have not reached the beginning of the exam, control returns back to step 104. If the beginning of the exam has been reached, then control proceeds to step 112 which marks the start of MRAC. In step 114 we go forward in time and construct a frame with 0.5 million events. In step 116 the frame is reconstructed and co-registered with the reference frame and the motion transfer function is recorded (for details see FIG. 2). In step 118 the last maximum 5 recent co-registered frames (till the start of MRAC) are used to average and update the reference frame. In step 120 the motion transfer functions are passed to any subsequent PET image reconstruction (dynamic or static) for motion correction.

Figure 2:
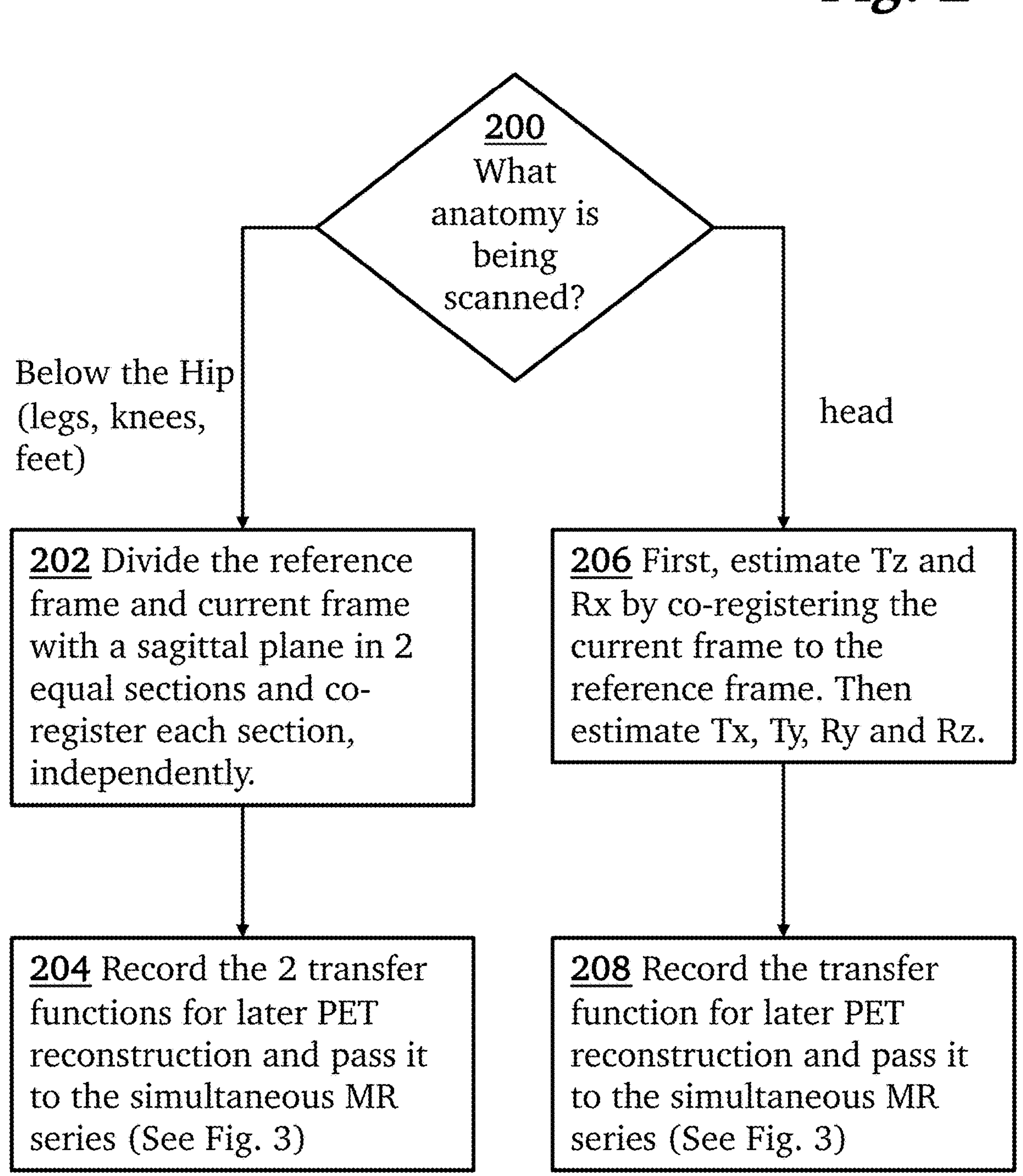
FIG. 2 is a flowchart outlining details of one part of a method for rigid motion correction, according to an embodiment of the invention.

FIG. 2 is a flowchart outlining details of steps 106 and 116 of the method for rigid motion correction outlined in FIG. 1. In step 200 the procedure splits into separate branches depending on the anatomy is being scanned, i.e., lower extremities (legs, knees, feet) or head. In step 202 for the lower extremities, the reference frame and current frame are divided with a sagittal plane in two equal sections and each section is co-registered, independently. In step 204 the two transfer functions for later PET reconstruction are recorded and passed to the simultaneous MR series (for details see FIG. 3) In step 206 for the head, Tz and Rx are estimated by co-registering the current frame to the reference frame. Then Tx, Ty, Ry and Rz are estimated. In step 208 the transfer function is recorded for later PET reconstruction and passed to the simultaneous MR series (for details see FIG. 3).

Figure 3:
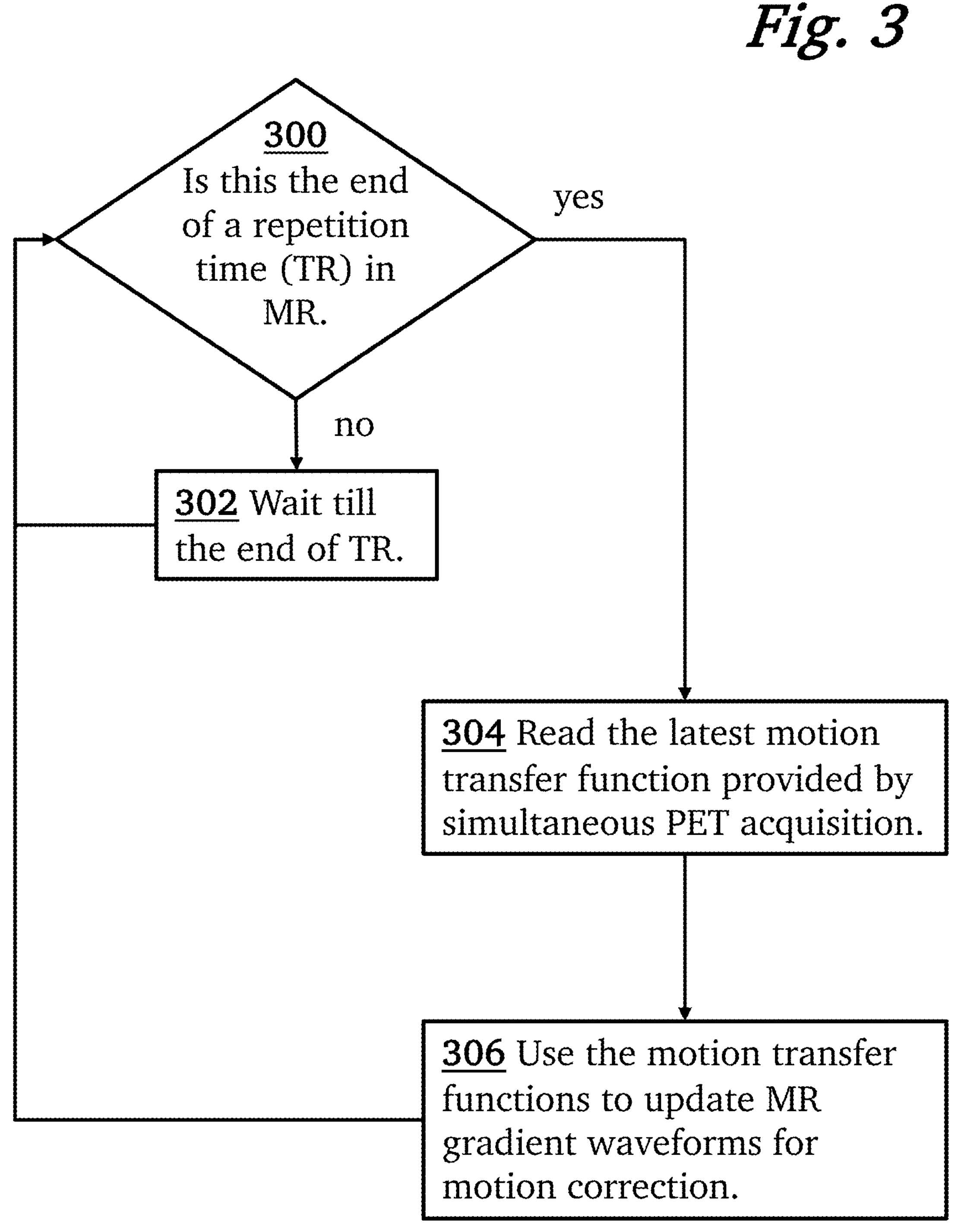
FIG. 3 is a flowchart outlining details of one part of a method for rigid motion correction, according to an embodiment of the invention.

FIG. 3 is a flowchart outlining details of a simultaneous MR series performed at the conclusion of the steps 204 and 208 of FIG. 2. In step 300 the process checks for the end of a repetition time (TR) in MR. In the case where the end of TR is not reached yet, in step 302 the process waits until the end of TR, and control then returns to step 300. If the end of TR has been reached, then in step 304 the latest motion transfer function provided by simultaneous PET acquisition is read. In step 306 the motion transfer functions is used to update MR gradient waveforms for motion correction. Control is then returned to step 300.

In an experiment to validate the method, a subject is injected with a 300 MBq of $^{18}$F-based PET tracer and underwent a one hour of brain PET/MR exam immediately after injection. PET data was divided into short frames, each containing 500,000 events. This ensured consistent image quality between frames for reliable motion estimation. A single frame of reference at the time of MR attenuation correction series was chosen from the early uptake and used for co-registering all other frames and the motion transfer function for each frame was estimated. Using the proposed method, the reference was updated dynamically with the most recent PET short frame images and then it was used for co-registering the next short frame to estimate the motion transfer function for that frame.

In another experiment to validate the method, another subject is injected with 180 MBq of $^{18}$F-NaF and underwent a 35 min of knee PET/MR exam immediately after injection. The PET data was divided into short frames, each holding 500,000 events, and a single reference frame was constructed at the time of the MR attenuation correction series. Both the reference frame and all PET frame images were divided into two equal sections using a sagittal plane. Each section of every PET frame was co-registered with its corresponding section on the reference frame. These sections were then used to update the reference frame, as proposed in our method.

Figure 4:
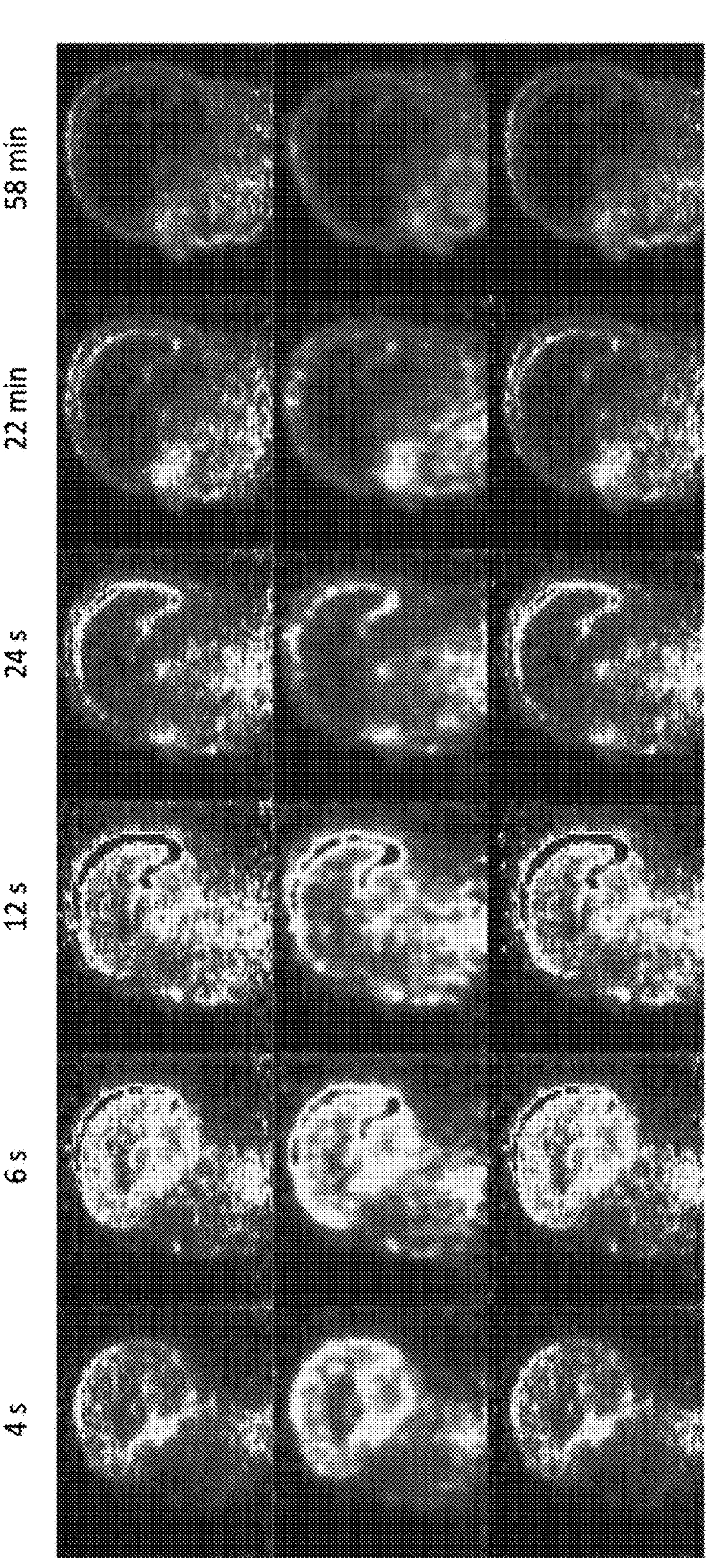
FIG. 4 is an image grid comparing single frame of reference with adaptive frame of reference in PET motion correction using a small set of images chosen at various time points after the injection.
Figure 5A:
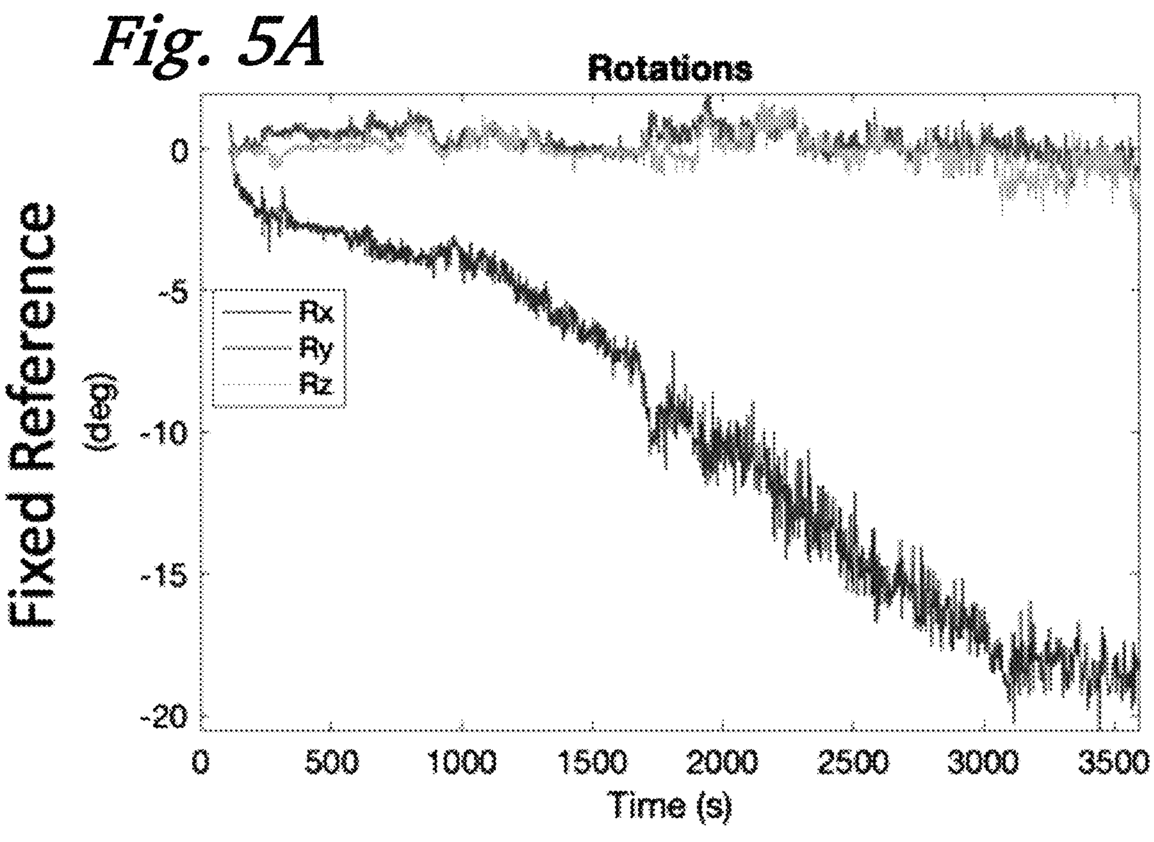
FIG. 5A is a graph of rotations in x, y, z directions vs time for a fixed single frame of reference in PET motion estimation.
Figure 5B:
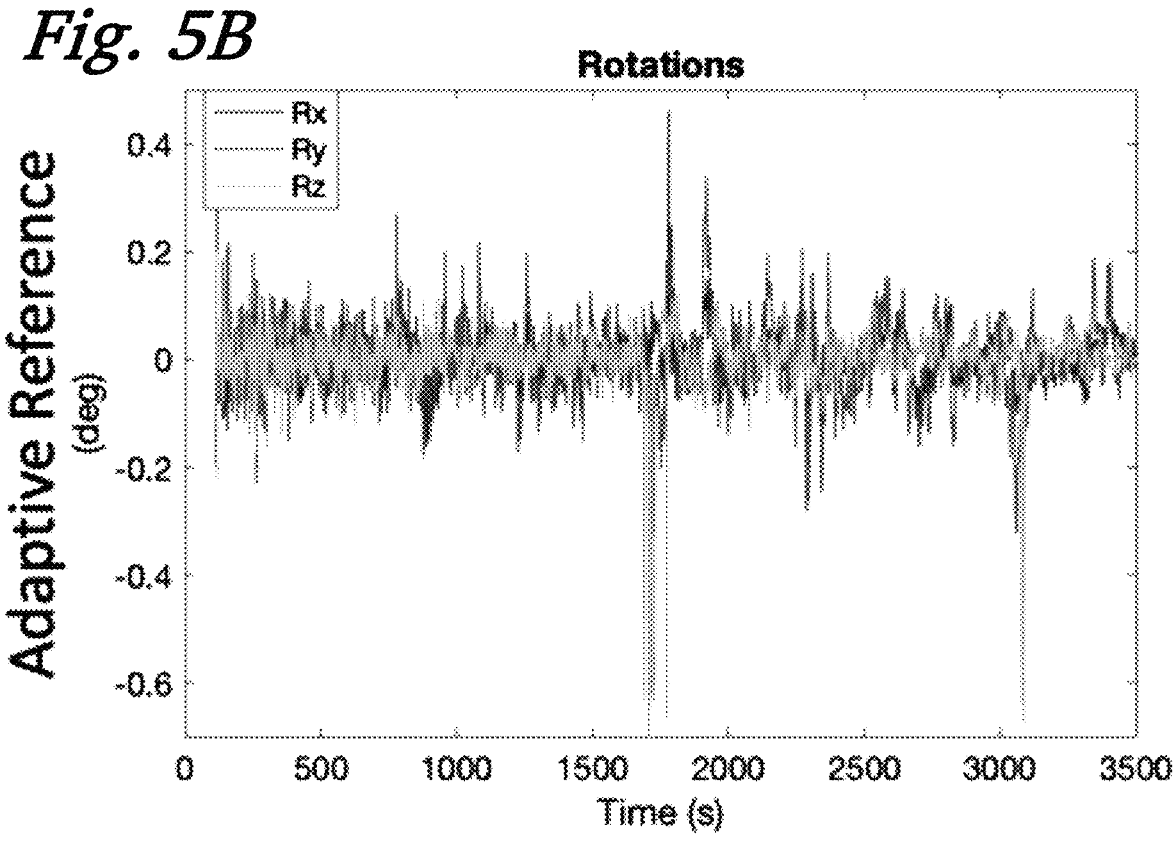
FIG. 5B is a graph of rotations in x, y, z directions vs time for an adaptive frame of reference in PET motion estimation.
Figures 5C, 5D:
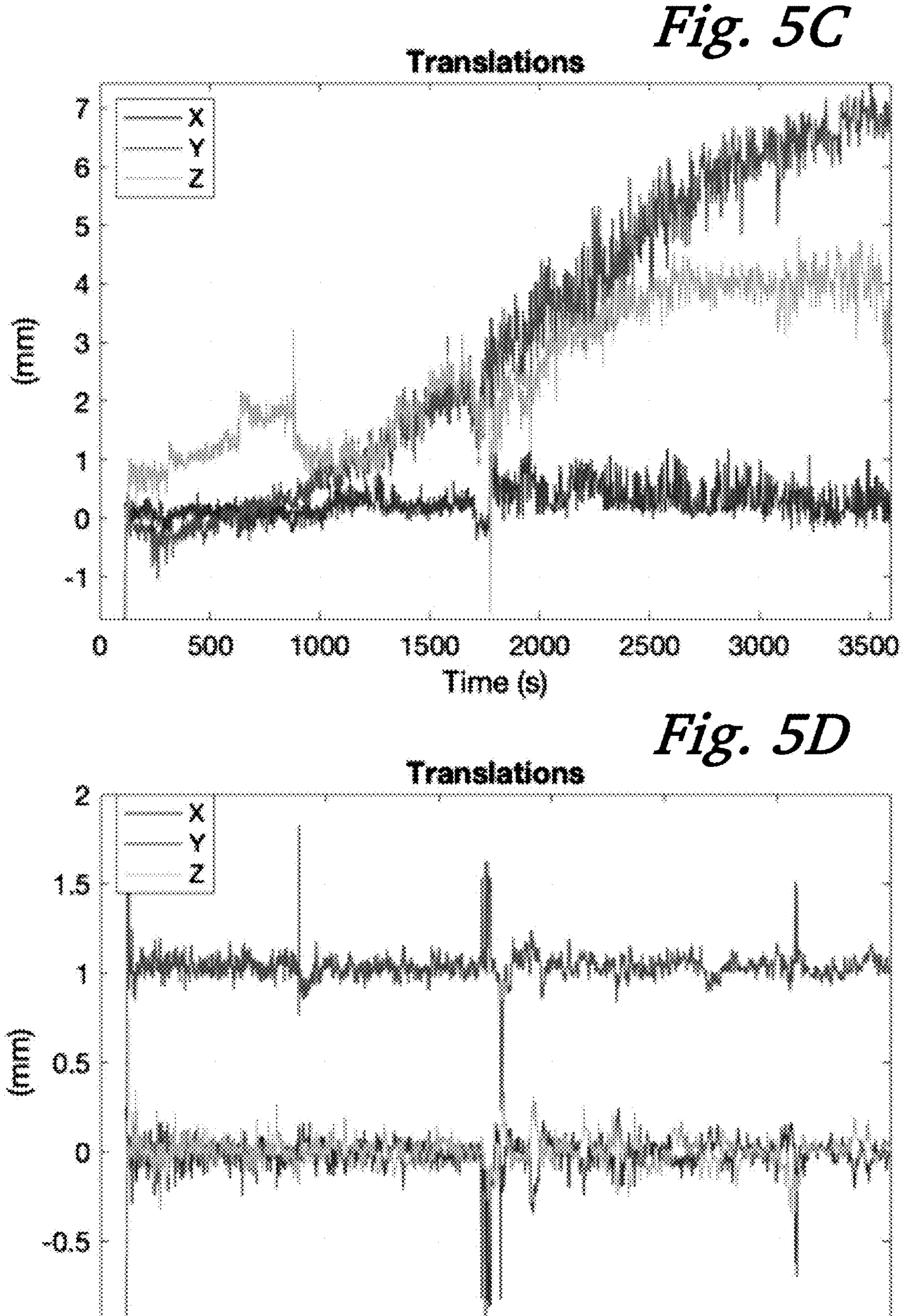
FIG. 5C is a graph of translations in x, y, z directions vs time for a fixed single frame of reference in PET motion estimation.
FIG. 5D is a graph of translations in x, y, z directions vs time for an adaptive frame of reference in PET motion estimation.
Figure 5E:
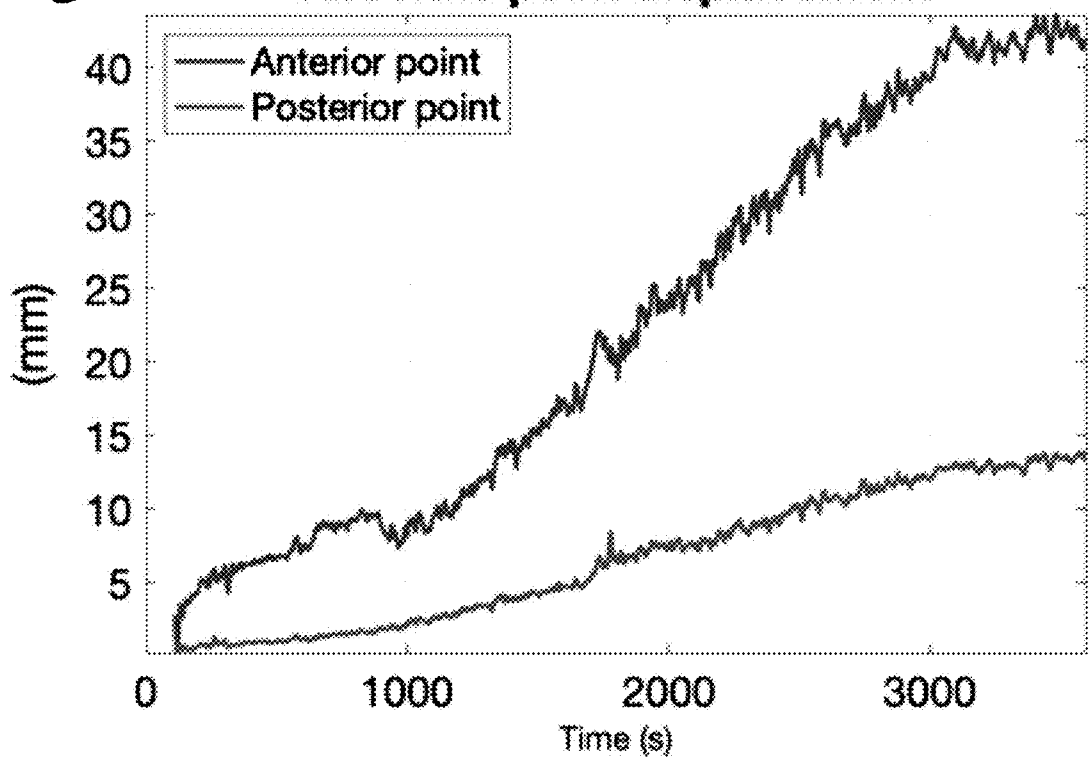
FIG. 5E is a graph of absolute anterior and posterior point displacements vs time for a fixed single frame of reference in PET motion estimation.
Figure 5F:
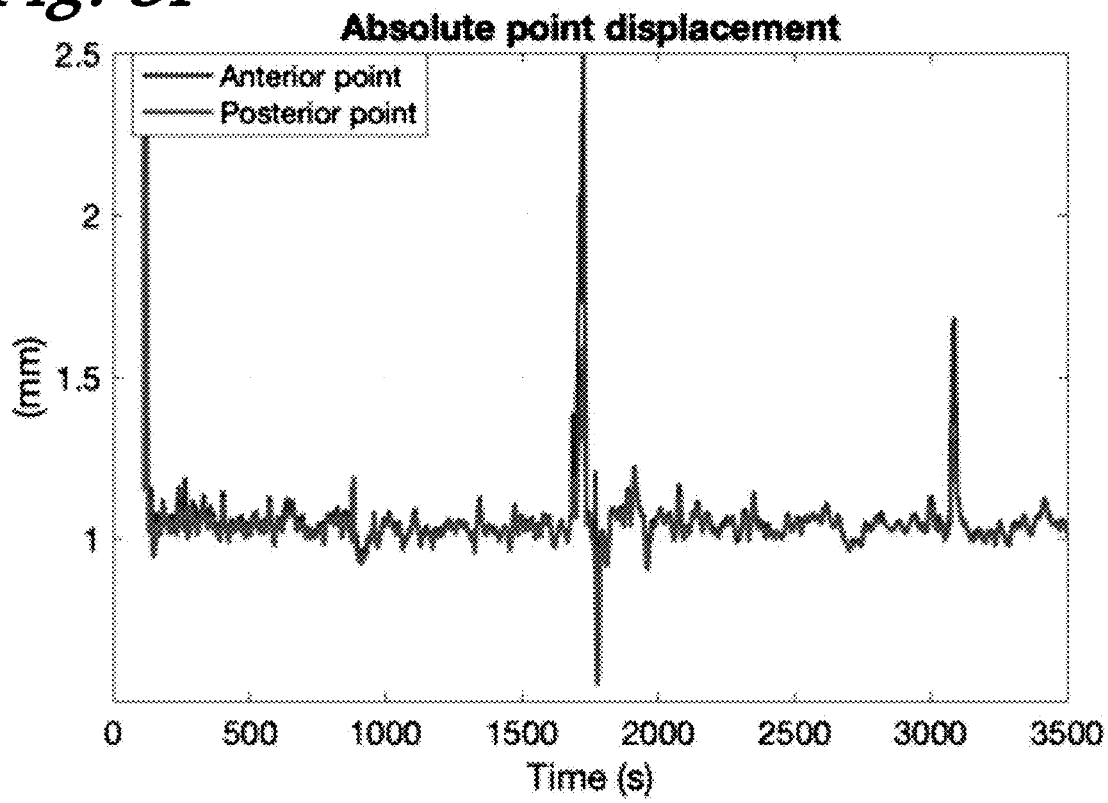
FIG. 5F is a graph of absolute anterior and posterior point displacements vs time for an adaptive frame of reference in PET motion estimation.
Figures 6A, 6B:
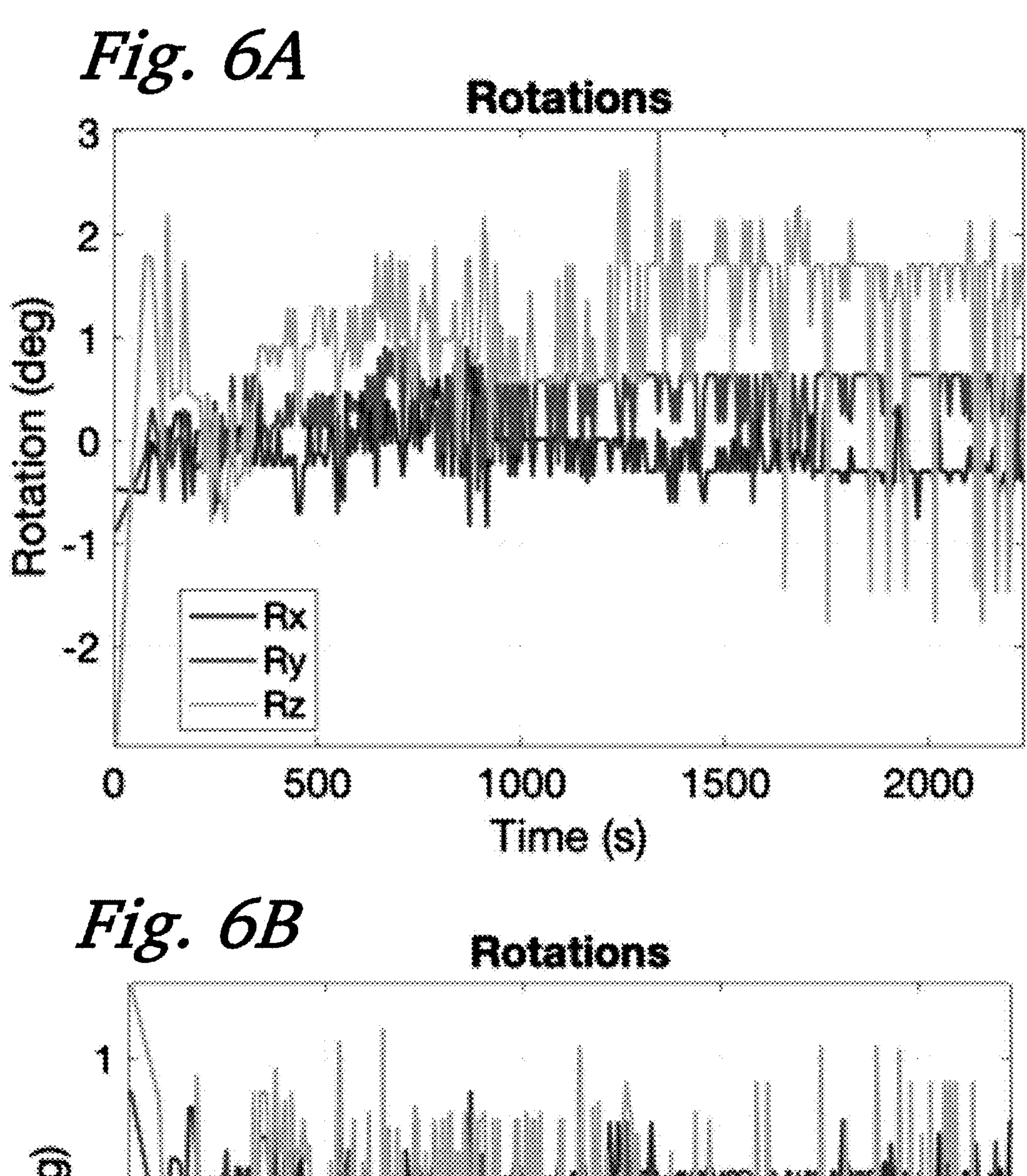
FIG. 6A is a graph of estimated rotational motion in x, y, z directions vs time for the right knee.
FIG. 6B is a graph of estimated rotational motion in x, y, z directions vs time for the left knee.
Figure 6C:
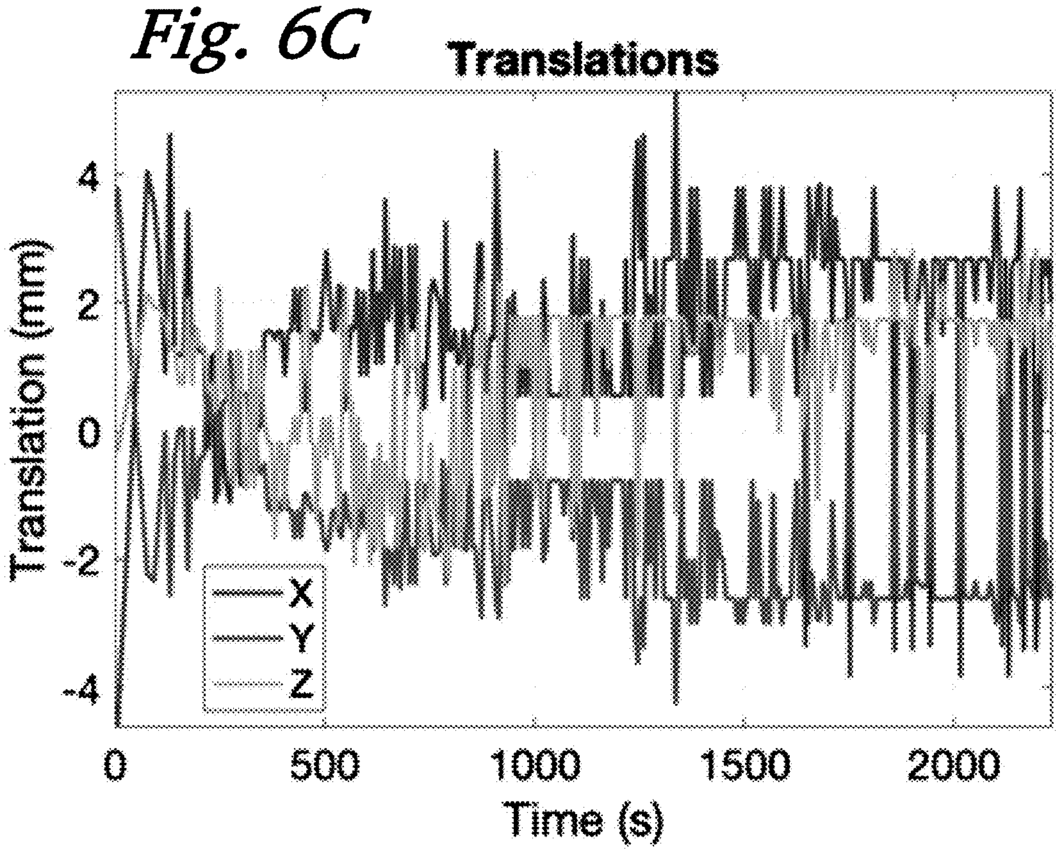
FIG. 6C is a graph of estimated translational motion in x, y, z directions vs time for the right knee.
Figure 6D:
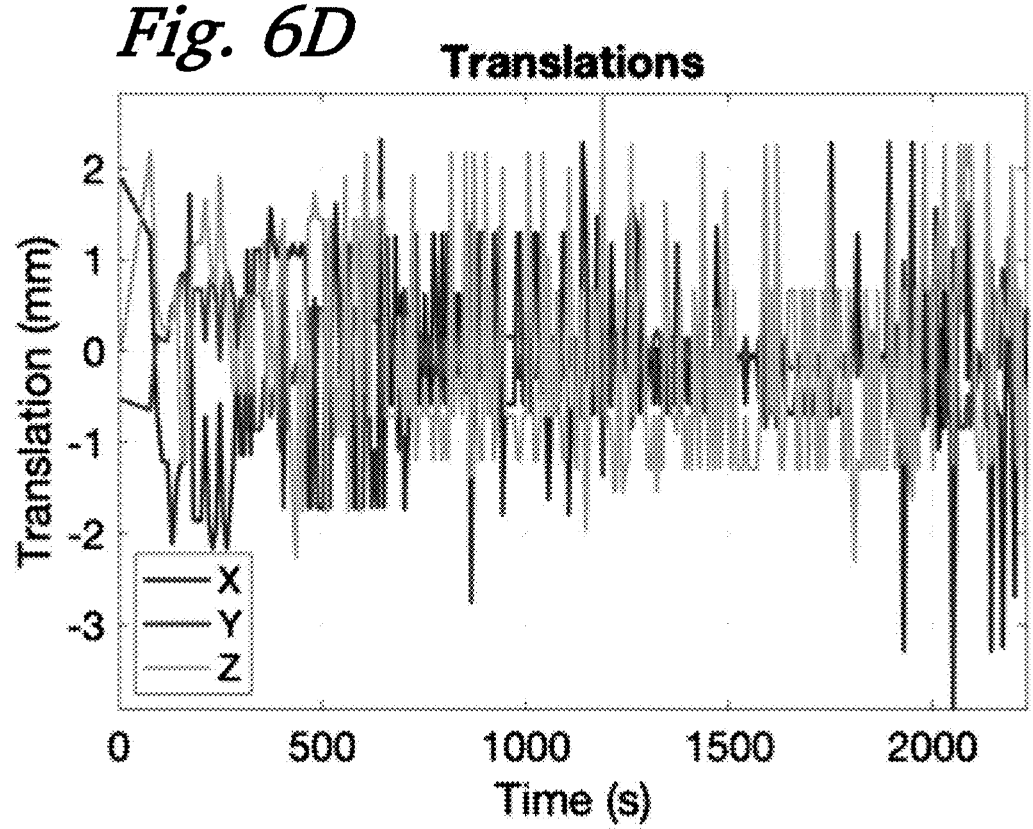
FIG. 6D is a graph of estimated translational motion in x, y, z directions vs time for the left knee.
Figure 6E:
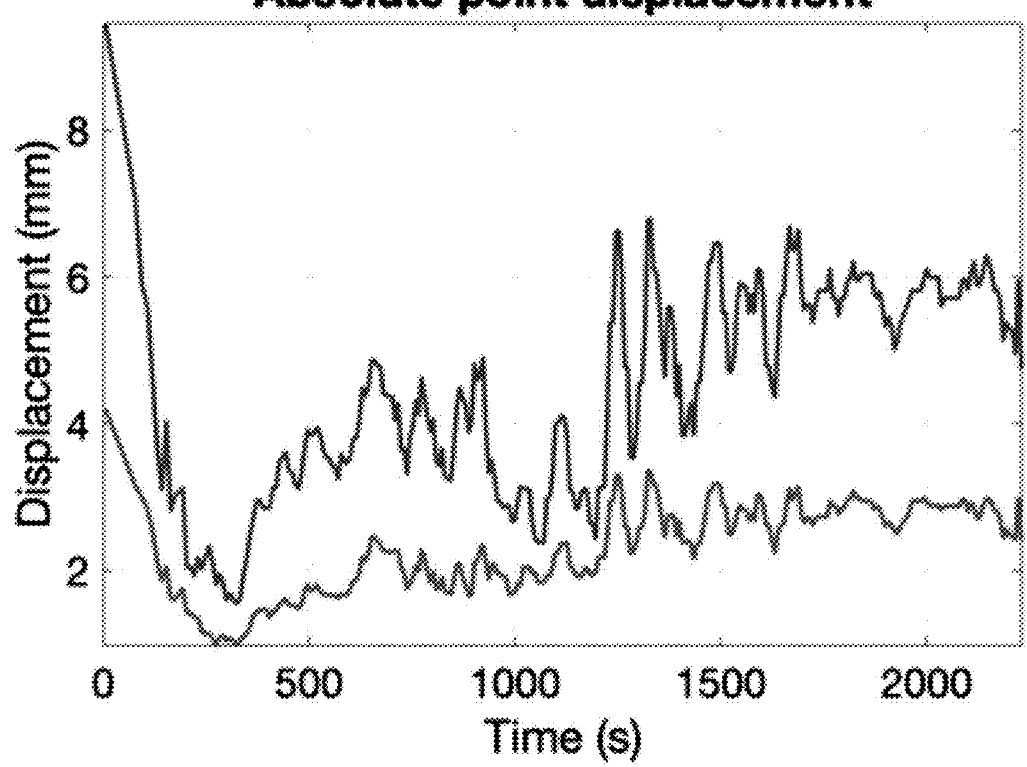
FIG. 6E is a graph of estimated absolute anterior and posterior point displacement vs time for the right knee.
Figure 6F:
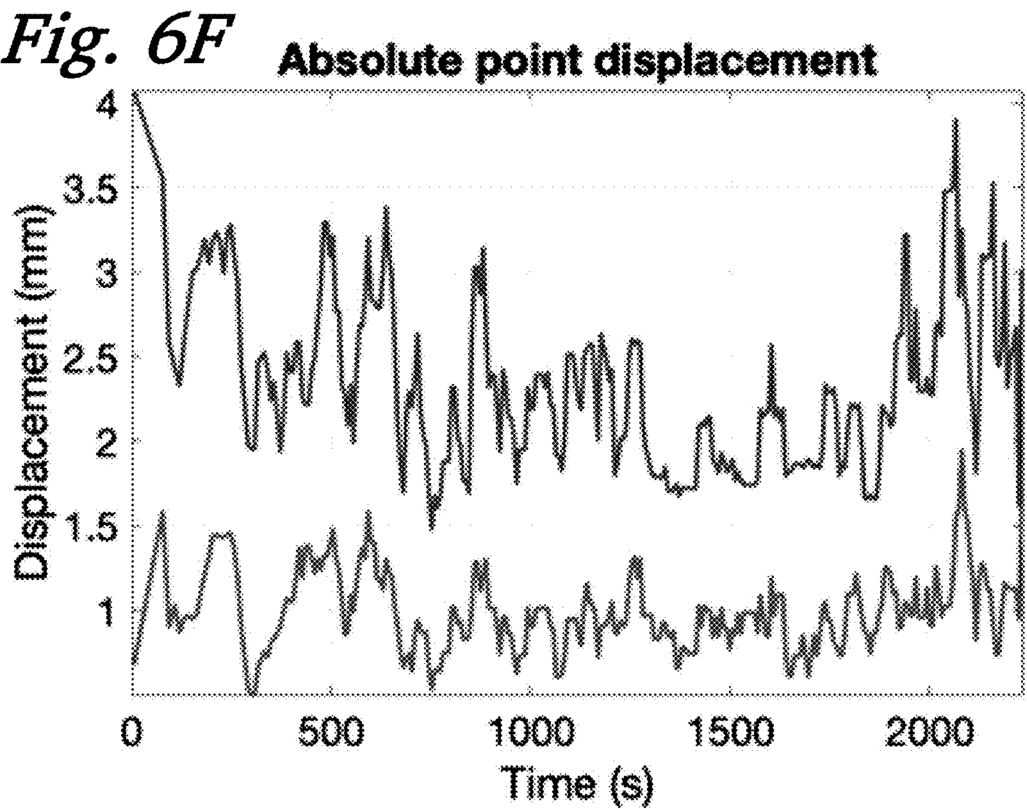
FIG. 6F is a graph of estimated absolute anterior and posterior point displacement vs time for the left knee.

FIG. 4 compares single frame of reference with adaptive frame of reference in PET motion correction using a small set of images chosen at various time points after the injection, shown in separate columns. The top row are original mages, the middle row are co-registered images using a fixed reference frame, and the bottom row are co-registered frames using an adaptive reference frame. The single frame of reference has miss registered the later frames (22 min and 58 min after the injection). As expected, the adaptive reference frame outperforms the single reference frame. The PET images for the single reference frame have been filtered for more robustness co-registration but it also affects the accuracy of co-registration. However, in our method both robustness and accuracy of co-registration process achieved by prioritizing Tz and Rx estimation. The single frame approach has failed to capture the patient's motion.

FIGS. 5A-5F compare single frame of reference with adaptive frame of reference in PET motion estimation. These figures show the motion transfer function (Tx, Ty, Tz, Rx, Ry, and Rz) through time. The single frame of reference has failed to capture the motion transfer function correctly.

FIGS. 6A-6F show estimated motion of right and left knees of a subject injected with 180 MBq of $^{18}$F-NaF. The motion transformer and also the absolute displacement of the tracker points are different for each knee. These figures show the motion transformation and the plots for two tracking points (each located 70 mm from the image's center) for both the right and left knees. The figure displays a unique pattern of motion for each knee, suggesting that the entire image cannot be treated as one rigid body. However, by dividing the image into two sections using a sagittal plane, we can treat each section as a rigid body and apply motion correction accordingly.

The invention claimed is:

1. A method for combined PET/MR imaging to correct for evolving tracer distribution during a scan, the method comprising: performing a dynamic PET/MR scan using a PET/MR scanner, wherein performing the dynamic PET/MR scan comprises:

a) iteratively reconstructing a plurality of frames frame and co-registering each the frame of the plurality of frames with a reference frame; and b) after each frame is co-registered, adaptively regenerating and dynamically updating the reference frame by incorporating multiple most recently co-registered images from previously reconstructed frames in the plurality of reconstructed frames.

2. The method of claim 1 wherein said iteratively reconstructing the frame and co-registering the frame comprises:

a) initially estimating translation along the Z-axis and translation along the X-axis by co-registering a current frame to the reference frame; and b) subsequently estimating translation along the Y-axis, rotation around the X-axis, rotation around the Y-axis, and rotation around the Z-axis.

3. The method of claim 1 wherein said iteratively reconstructing the plurality of frames and said co-registering each frame of the plurality of frames comprises:

a) dividing the reference frame with a sagittal plane in two equal sections, and b) independently co-registering each of the two equal sections.

4. The method of claim 1 wherein said dynamically updating the reference frame comprises estimating a motion transfer function from short PET frames live on the PET/MR scanner and using the motion transfer function in an MRI sequence to update gradient waveforms and correct for patient motion.

* * * * *